(12) United States Patent
Khoury

(10) Patent No.: US 9,205,237 B2
(45) Date of Patent: Dec. 8, 2015

(54) SINGLE LUMEN DISTAL PERFUSION SHEATH

(71) Applicant: Michael D. Khoury, St. George, UT (US)

(72) Inventor: Michael D. Khoury, St. George, UT (US)

(73) Assignee: KHOURY MEDICAL DEVICES, LLC, Saint George, UT (US)

( * ) Notice: Subject to any disclaimer, the term of this patent is extended or adjusted under 35 U.S.C. 154(b) by 212 days.

(21) Appl. No.: 14/033,058

(22) Filed: Sep. 20, 2013

(65) Prior Publication Data

US 2014/0024994 A1 Jan. 23, 2014

Related U.S. Application Data

(63) Continuation-in-part of application No. 13/548,458, filed on Jul. 13, 2012, now Pat. No. 9,017,275, and a continuation-in-part of application No. 13/549,465, filed on Jul. 14, 2012, now Pat. No. 8,728,011.

(60) Provisional application No. 61/507,492, filed on Jul. 13, 2011, provisional application No. 61/510,786, filed on Jul. 22, 2011.

(51) Int. Cl.

| *A61B 19/00* | (2006.01) |
|---|---|
| *A61M 27/00* | (2006.01) |
| *A61F 2/02* | (2006.01) |
| *A61F 2/06* | (2013.01) |
| *A61B 1/00* | (2006.01) |

(52) U.S. Cl.
CPC .......... *A61M 27/002* (2013.01); *A61B 1/00135* (2013.01); *A61F 2/02* (2013.01); *A61F 2/06* (2013.01); *A61F 2/064* (2013.01); *A61F 2002/061* (2013.01); *A61F 2002/065* (2013.01)

(58) Field of Classification Search
CPC ............ A61F 2002/061; A61F 2/006; A61M 27/002; A61M 25/0026; A61M 25/0028; A61M 2025/004; A61M 25/0043; A61M 25/001; A61M 25/005
USPC ........................ 604/8, 9, 264, 507, 167.3, 539
See application file for complete search history.

(56) References Cited

U.S. PATENT DOCUMENTS

| 4,540,402 | A | 9/1985 | Aigner |
| 5,284,473 | A | 2/1994 | Calabria |
| 5,876,367 | A | 3/1999 | Kaganov et al. |
| 5,879,321 | A * | 3/1999 | Hill .................................. 604/8 |
| 6,161,547 | A | 12/2000 | Barbut |
| 6,508,777 | B1 | 1/2003 | Macoviak et al. |
| 6,579,311 | B1 | 6/2003 | Makower |
| 7,628,768 | B2 * | 12/2009 | Faul et al. ........................ 604/8 |

* cited by examiner

*Primary Examiner* — Leslie Deak
(74) *Attorney, Agent, or Firm* — Blue Filament Law PLLC; Avery N. Goldstein

(57) ABSTRACT

A distal perfusion sheath (DPS) is provided for cases where blood perfusion is needed for downstream arteries (distal) to the insertion point of the DPS within the target artery. The ability to provide distal perfusion with the DPS allows the DPS to be positioned in the target artery for long periods without causing lack of blood flow (ischemia) to an extremity that the target artery supplies. In certain embodiments, the DPS can still be used for surgical arterial access while allowing blood flow downstream. In addition, embodiments of the DPS configured with longer perfusion shunts can allow a contra-lateral extremity downstream to a large DPS to have blood flow while the sheath is in place.

13 Claims, 7 Drawing Sheets ated Sep. 20, 2012,
which are incorporated herein by reference.

SINGLE LUMEN DISTAL PERFUSION SHEATH

CROSS-REFERENCE TO RELATED APPLICATION

This application is a continuation in part of Non-provisional application Ser. No. 13/548,458 filed Jul. 13, 2012 that claims priority benefit of U.S. Provisional Application Ser. Nos. 61/507,492 filed Jul. 13, 2011 and 61/510,786 filed Jul. 22, 2011; and is a continuation in part of Non-provisional application Ser. No. 13/549,465 filed Jul. 14, 2012 that in turn claims priority to U.S. Provisional Application Ser. No. 61/510,786, filed Jul. 22, 2011; and is a Non-provisional Application that claims priority benefit of U.S. Provisional Patent Application Ser. No. 61/703,757 filed Sep. 20, 2012, which are incorporated herein by reference.

FIELD OF THE INVENTION

The present invention in general relates to arterial sheaths and method for surgical deployment thereof, and in particular to a vascular sheath that facilitates blood perfusion to a distal artery thereby preventing ischemia to the extremity the artery supplies.

BACKGROUND OF THE INVENTION

As endovascular procedures become more complicated, the procedures often take longer to perform and often require larger sheaths to be in a patient's arteries for extended periods of time. However, larger surgical sheaths impair blood flow to a distal extremity and can cause injury to the nerves and muscles. In addition, after prolonged lack of blood flow (ischemia) the extremity is at risk for re-perfusion injury once the sheath is removed that can increase muscle compartment pressures (compartment syndrome), which can result in muscle necrosis and amputation.

Thus, there exists a need for a vascular surgical sheath that allows continued blood flow past the insertion point of the sheath, while the sheath is in place, to an extremity downstream to the sheath. There further exists a need for a process for usage of such a sheath to inhibit compartment syndrome.

SUMMARY OF THE INVENTION

An inventive distal perfusion sheath (DPS) is provided for cases where blood perfusion is needed for downstream arteries (distal) to the insertion point of the DPS within the target artery. The ability to provide distal perfusion with the DPS allows the DPS to be positioned in the target artery for long periods without causing lack of blood flow (ischemia) to an extremity that the target artery supplies. In specific embodiments, the DPS is used for surgical arterial access while allowing blood flow downstream. In addition, embodiments of the DPS configured with longer perfusion shunts can allow a contra-lateral extremity downstream to a large DPS to have blood flow while the sheath is in place.

Embodiments of the DPS have a single lumen for arterial access while also providing blood flow into the attached perfusion shunt. The lumen allows arterial blood to flow through a perfusion shunt that is attached to the external distal end of the sheath. The end of the perfusion shunt may then be inserted into an artery downstream (distal) to the sheath providing blood flow to the extremity. The insertion of the perfusion shunt can be accomplished by making a small incision (arteriotomy) in the artery just below the sheath. The end of the perfusion shunt is then placed into the artery and secured with a vessel loop. The insertion of the perfusion shunt into a distal portion of the artery allows continued blood flow into the artery downstream from the sheath. At the end of the surgical procedure the perfusion shunt is removed and the incision in the distal artery is repaired.

In an embodiment, in cases that require large specialized sheaths, downstream flow can be provided by placing a distal perfusion sheath in the opposite extremity artery. The distal perfusion sheath can be small enough to allow continued blood flow to the downstream extremity. The perfusion shunt can then be inserted into the artery just below the opposite sheath to provide blood flow to the opposite extremity.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DESCRIPTION OF THE PREFERRED EMBODIMENTS

The present invention has utility in vascular surgery and in particular to a vascular sheath that promotes perfusion during a procedure so as to promote cellular metabolism of distal tissues. Improved surgical outcomes are noted with resort to the inventive sheath and usage thereof.

Traditionally, the placement of sheaths in an artery decreases or eliminates blood flow distal (around) the sheath to the distal organ that is fed by the subject artery. Although the sheath may be in the artery for long periods of time, the actual delivery of surgical devices through the sheath is for a minor fraction of the sheath insertion time. Therefore, the majority of the time the working lumen of the sheath is used to provide blood flow to the distal perfusion shunt of the inventive sheath, thereby allowing blood flow to the distal extremity for the majority of time the sheath is positioned in the artery. It is appreciated that while an inventive DPS blood flow can be partially or fully interrupted during the delivery of the vascular devices this represents only a small fraction of the total time that the sheath is positioned in the subject artery. The time in which the blood flow is occluded during the delivery of vascular devices is generally well tolerated by the effected downstream tissues. The effected tissue is then supplied with blood through the perfusion shunt with the removal of the vascular devices.

In specific inventive embodiments, such as in cases that require large specialized sheaths, downstream blood flow is provided by placing a distal perfusion sheath in the opposite extremity artery. The distal perfusion sheath is sized to allow continued blood flow to the downstream extremity. The perfusion shunt can then be inserted into the artery just below the opposite sheath to provide blood flow to the opposite extremity. The inventive sheath is readily constructed with biocompatible polyurethane materials, with possible metal, or Nitinol reinforcement. It is appreciated that an inventive sheath optionally and readily incorporates substances such as radio opaque marking compounds on the catheter for accurate positioning such as barium sulfate; slip agents for smooth artery entry such as hydrophilic gels sold under that trade name GLIDEX®; anticoagulants such as heparin; sustained release drugs such as antibiotics and plaque formation inhibitors; and combinations thereof.

Figure 1A:
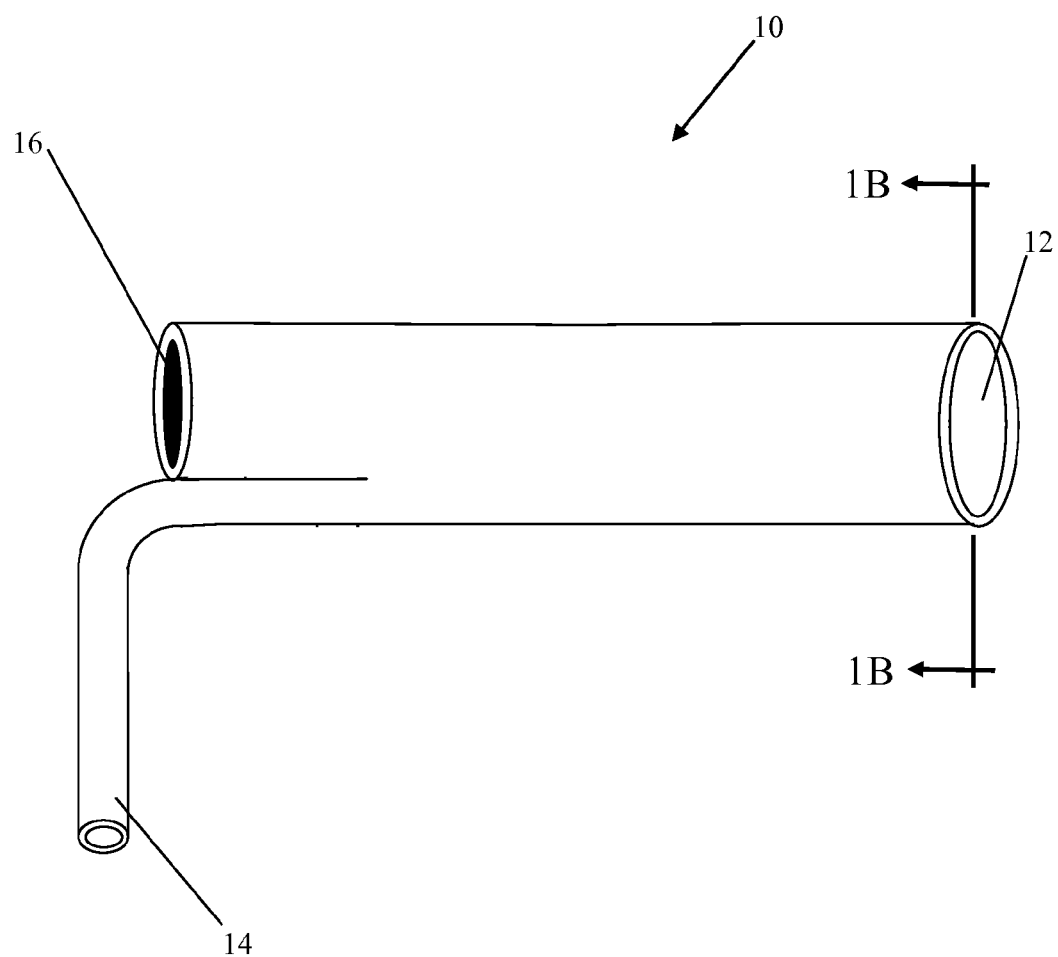
FIG. 1A is a perspective view of an inventive distal perfusion sheath (DPS) device.
Figure 1B:
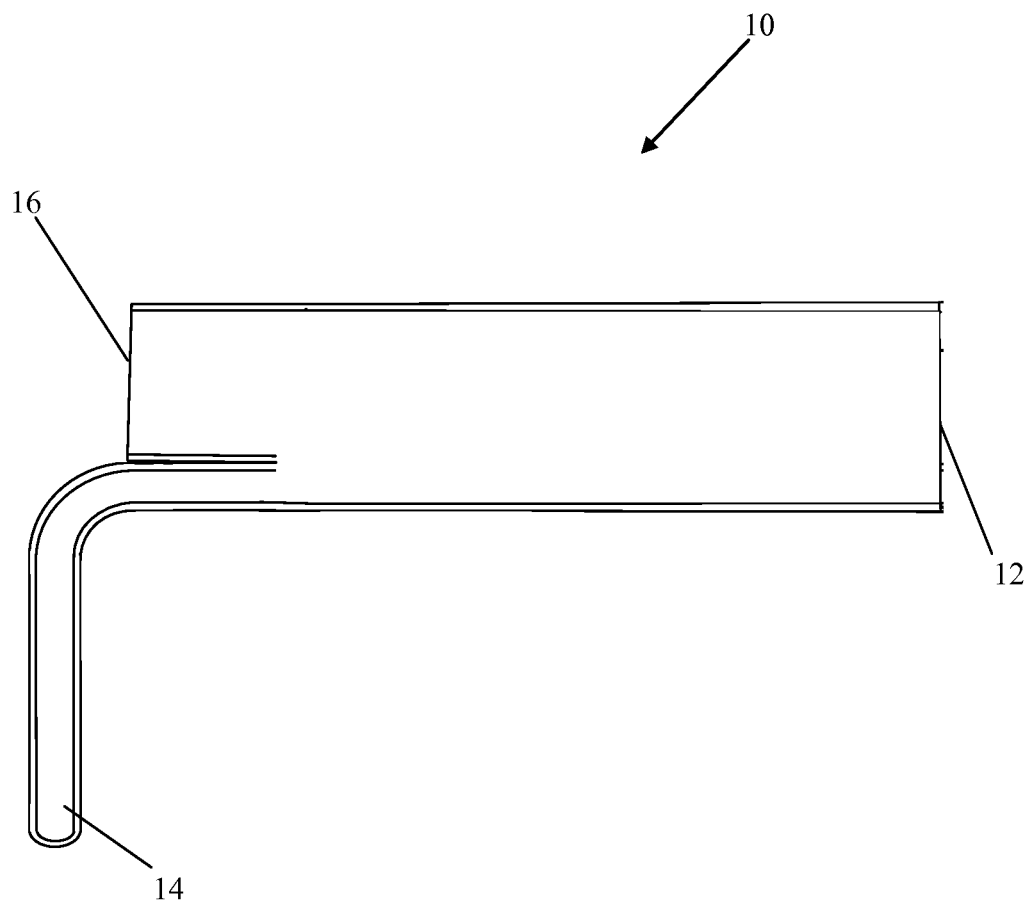
FIG. 1B is a longitudinal cross-sectional view of the device of FIG. 1A along line 1B-1B.

Referring now to FIGS. 1 and 2, an inventive distal perfusion sheath (DPS) is depicted generally at 10. The DPS 10 includes a lumen 12 for arterial access and a perfusion shunt 14 for providing blood flow to a distal artery. Hemostatic port 16 controls blood flow in the lumen 12, and allows for insertion of a catheter, guide wire, camera, or other surgical device into the artery V.

Figure 2A:
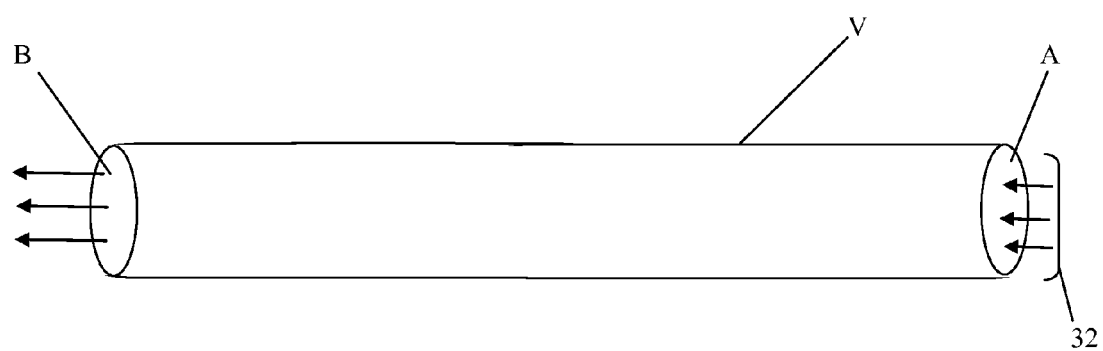
FIG. 2A is a perspective view of an artery prior to the insertion of a sheath.
Figure 2B:
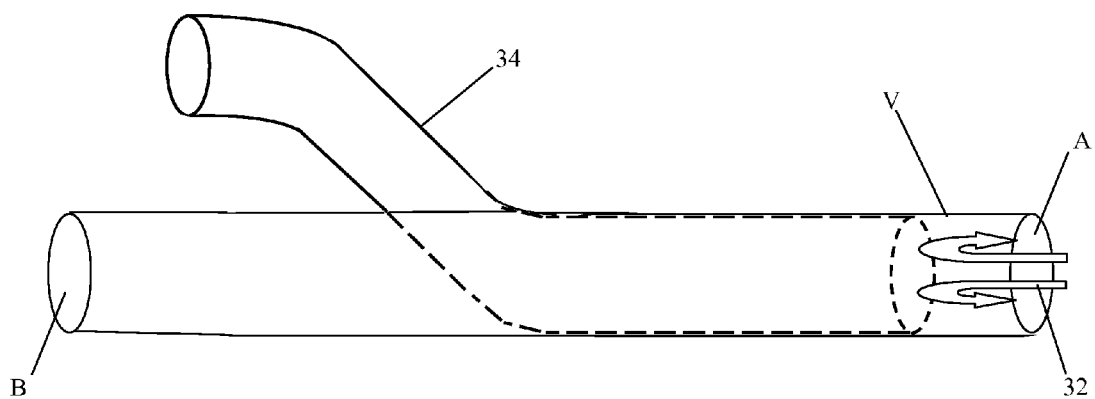
FIG. 2B is a perspective view of an artery with a conventional prior art sheath inserted, and the resultant impaired blood flow in the artery.
Figure 2C:
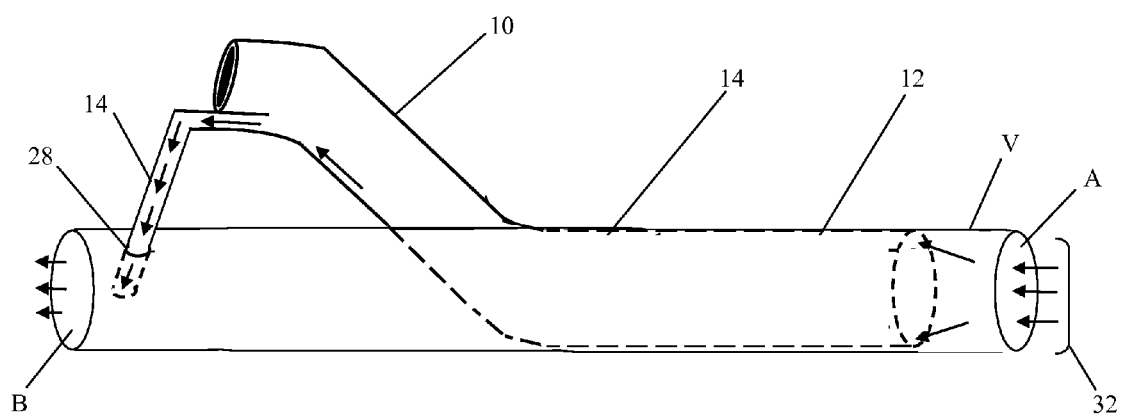
FIG. 2C is a perspective view of an artery with the inventive distal perfusion sheath inserted that allows blood flow past the sheath.

FIG. 2A depicts an artery V prior to the insertion of a sheath. Prior to the insertion of a sheath blood flow 32 is relatively unimpeded from proximal end A to distal end B. In FIG. 2B, a conventional sheath 34 is inserted in artery V with a resultant impairment of blood or fluid flow 32 from proximal end A to distal end B. In a similar manner in FIG. 2C, an embodiment of the DPS 10, with the perfusion shunt 14 inserted into artery V through incision 28 allowing blood flow 32 from proximal end A to distal end B. Thus as shown in FIG. 2C with the DPS 10 fully deployed and perfusion shunt 24 inserted in the distal portion of artery V, blood flow is rerouted beyond the DPS 10.

FIGS. 3 and 4A-4D illustrate an embodiment of a distal perfusion sheath (DPS) 40 employing multiple guidewires (42a, 42b, 42c) for implementations where simultaneous guidewire access to multiple target arteries is required without disrupting blood flow to a distal bodily extremity that the artery supplies. An engagement system (44a, 44b, 44c) independently secures the one or more guidewires within the sheath of the DPS 40 to maintain the separate positions of the guidewires. The engagement system (44a, 44b, 44c) is a series of wire-lock engagement points (44a, 44b, 44c) positioned along for example, the circumference of an inventive sheath. Selection of a guidewire is made with a rotating hub 46 with a hemostatic port 16 at the center.

In operation, the rotation of the hub 46 at the distal end of the DPS allows the slit 48 of the hemostatic port 16 to line up with a desired wire-lock (44a, 44b, 44c) of the engagement system to allow the guidewire to be positioned in and out of the wire-lock. When the locked guidewire is to be used in the main sheath lumen 12 of the DPS 40, the hub 46 is rotated to line up the valve-slit with the guidewire in the wire-lock. The lock is opened releasing the guidewire which is then moved through the valve-slit to the center hub of the hemostatic valve and then used in a conventional manner in a target artery. Following the usage of the unlocked guidewire, the guidewire is returned through the valve-slit to the wire-lock to be reengaged. The wire-lock when closed secures the guidewire in place preventing it from being dislodged while the lumen 12 of the sheath is used with other guidewires. The hub 46 may then be rotated to line up the valve-slit 48 with another wire-lock to access a different guidewire for serving the same or different target artery.

Figure 3:
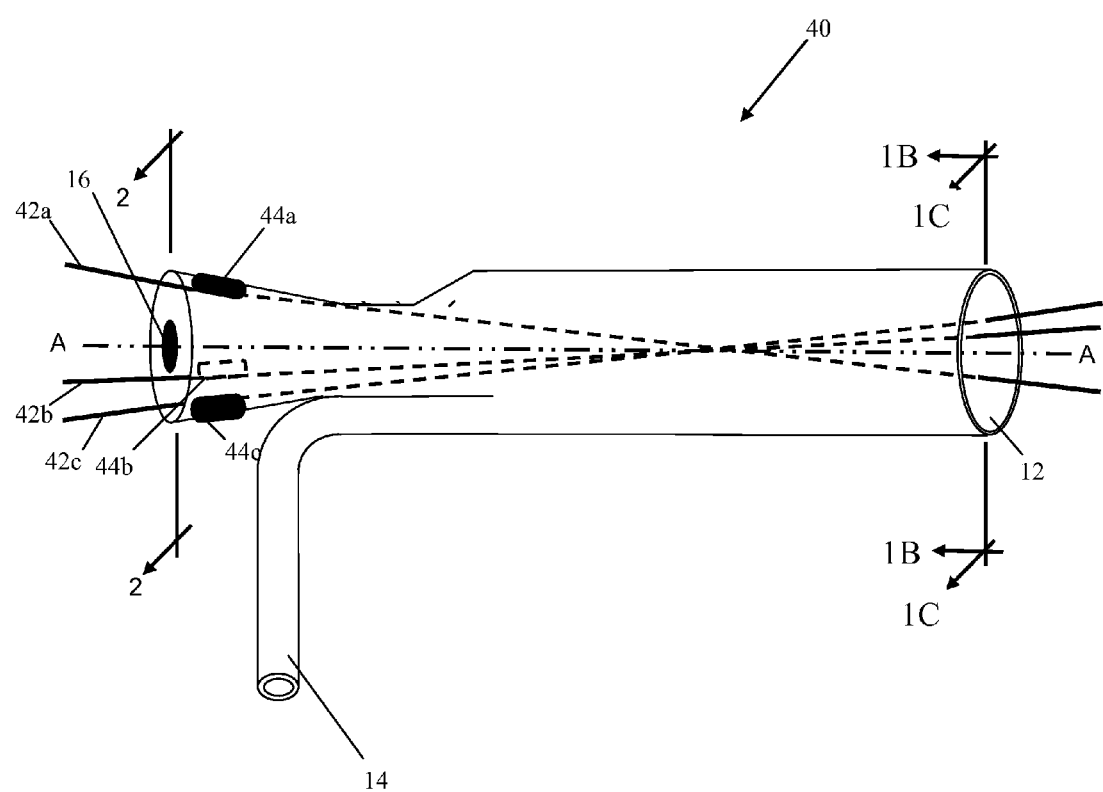
FIG. 3 is a perspective view of an embodiment of an inventive distal perfusion sheath configured with multiple guidewires in the sheath.
Figure 4A:
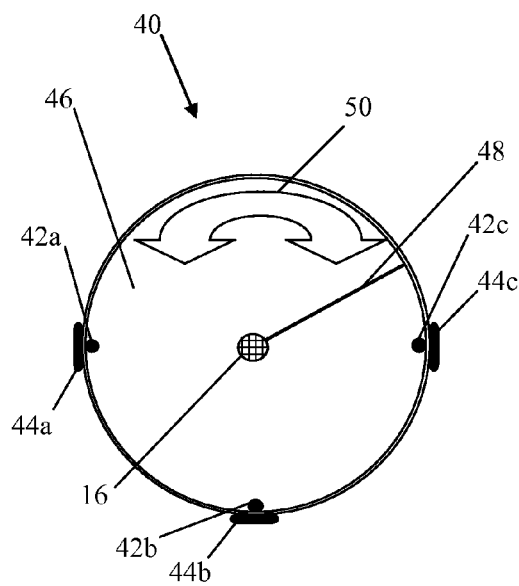
FIGS. 4A-4D are a series of cross-sectional views of the device of FIG. 3 along line 2-2 illustrating the unlocking and repositioning of a guidewire from amongst the three guidewires in the sheath.
Figure 4B:
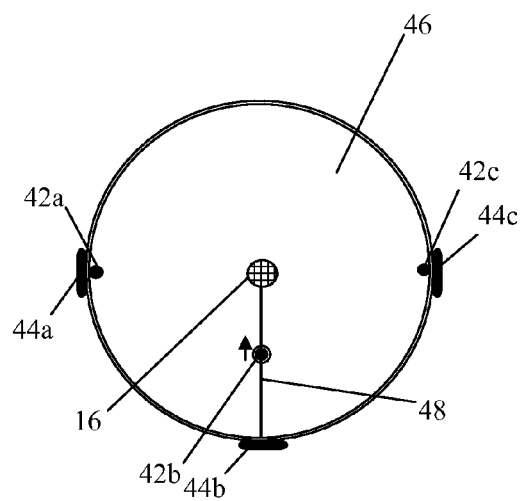
Figure 4C:
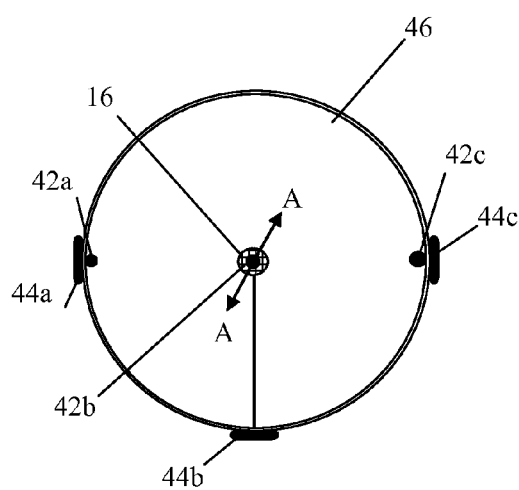
Figure 4D:
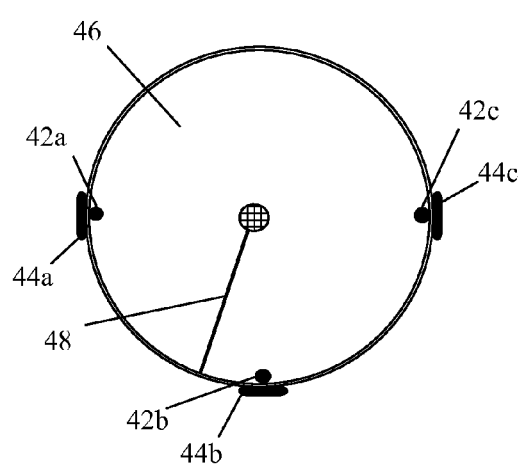

FIGS. 4A-4D are a series of cross-sectional views of the DPS device 40 of FIG. 3 along line 2-2 illustrating the unlocking and repositioning of the guidewire 42b. In FIG. 2A, all three of the guidewires (42a, 42b, 42c) are secured or locked to the engagement system (44a, 44b, 44c). In FIG. 4B, the rotating hub 46, which is free to rotate either clockwise or counter-clockwise as indicated by the bidirectional arrow 50, is rotated to position the slit 48 to line up with engagement 44b, and the guidewire 42b is unlocked from engagement 44b and moved inward toward the hemostatic valve seal port 16 in the center of the rotating hub 46. In FIG. 4C, the guidewire 42b is now positioned within the hemostatic valve seal port 16, and the guidewire is now free to move back and forth, or be twisted, along the longitudinal axis A-A of DPS device 40. In FIG. 4D, the guidewire 42b is returned to engagement 44b, and locked in place. The rotating hub 46 and corresponding slit 48 are now free to be rotated to another of the engagement 44a or 44c for using guidewires 42a or 42c, respectively.

The foregoing description is illustrative of particular embodiments of the invention, but is not meant to be a limitation upon the practice thereof. The following claims, including all equivalents thereof, are intended to define the scope of the invention.

The invention claimed is:

1. A sheath for insertion into an artery, said sheath comprising:
   a lumen with a proximal end configured for insertion into said artery, and a distal end that tapers outward;
   a perfusion shunt in fluid communication with said lumen, said perfusion shunt configured for insertion into a distal portion of said artery beyond said sheath to provide blood flow from a proximal portion of said artery prior to said inserted sheath to said distal portion of said artery;
   a plurality of guidewires within said lumen;
   an engagement system with a series of wire-lock engagement points affixed to said distal end for individually engaging each of said plurality of guidewires; and
   a rotatable hub at said distal end centered on a longitudinal axis of said sheath configured with a hemostatic valve at said center and a slit extending from said hemostatic valve to an outer edge of said hub.

2. The sheath of claim 1 wherein each of said plurality of guidewires is individually adjustable.

3. The sheath of claim 1 wherein a guidewire from said plurality of guidewires is adjustable when said slit is aligned with an engagement point corresponding to said guidewire, and the engagement point is unlocked to provide movement of said guidewire to said hemostatic valve via said slit.

4. The sheath of claim 1 wherein in the event said guidewire is positioned in said hemostatic valve, said guidewire is free to move back and forth, or be twisted, along a longitudinal axis of said sheath.

5. The sheath of claim 1 wherein said plurality of guidewires when engaged in said series of wire-lock engagement points are prevented from being dislodged when one guidewire from one of said plurality of guidewires is being used in said sheath.

6. The sheath of claim 1 wherein said engagement system secures said plurality of guidewires in independent positions in multiple target arteries.

7. The sheath of claim 1 wherein said sheath is constructed with biocompatible polyurethane materials.

8. The sheath of claim 7 wherein said biocompatible polyurethane materials are reinforced.

9. A method of using a sheath comprising:
inserting a sheath in a patient artery, said sheath comprising: a lumen with a proximal end configured for insertion into said artery, and a distal end that tapers outward; a perfusion shunt in fluid communication with said lumen, said perfusion shunt configured for insertion into a distal portion of said artery beyond said sheath to provide blood flow from a proximal portion of said artery prior to said inserted sheath to said distal portion of said artery; a plurality of guidewires within said lumen; an engagement system with a series of wire-lock engagement points affixed to said distal end for individually engaging each of said plurality of guidewires; and a rotatable hub at said distal end centered on a longitudinal axis of said sheath configured with a hemostatic valve at said center and a slit extending from said hemostatic valve to an outer edge of said hub;
inserting said perfusion shunt in said distal portion of said artery with a small incision (arteriotomy) in said distal portion of said artery just below said sheath; and
securing said perfusion shunt to said distal portion of said artery with a vessel loop.

10. The method of claim 9 further comprising:
rotating said hub until said slit is aligned with an engagement of said series of wire-lock engagement points;
unlocking a guidewire from said plurality of guidewires from said engagement corresponding to said engagement aligned with said slit; and
moving said unlocked guidewire along said slit to said hemostatic valve.

11. The method of claim 10 wherein in the event said guidewire is positioned in said hemostatic valve, said guidewire is free to move back and forth, or be twisted, along a longitudinal axis of said sheath.

12. The method of claim 10 wherein said plurality of guidewires when engaged in said series of wire-lock engagement points are prevented from being dislodged when said guidewire from said plurality of guidewires is being used in said sheath.

13. The method of claim 9 wherein said engagement system secures said plurality of guidewires in independent positions in multiple target arteries.

* * * * *